United States Patent [19]

Drabb, Jr.

[11] Patent Number: 4,906,781

[45] Date of Patent: Mar. 6, 1990

[54] METHOD FOR THE PREPARATION OF 4'-(SUBSTITUTED)-AMINO-2-(SUBSTITUTED) AMINO-3',5'-DICHLOROACETOPHENONE AND SALTS THEREOF

[75] Inventor: Thomas W. Drabb, Jr., Trenton, N.J.

[73] Assignee: American Cyanamid Company, Stamford, Conn.

[21] Appl. No.: 301,580

[22] Filed: Jan. 24, 1989

Related U.S. Application Data

[63] Continuation of Ser. No. 462,745, Feb. 1, 1983, abandoned.

[51] Int. Cl.$^4$ ............................................. C07C 97/10
[52] U.S. Cl. ................................... 564/343; 584/345; 584/365; 584/412
[58] Field of Search ............... 564/343, 345, 365, 412

[56] References Cited

U.S. PATENT DOCUMENTS 2,675,409  4/1954  Orloff et al. .................... 564/412
3,536,712  10/1970  Keck et al. ..................... 564/364 X

FOREIGN PATENT DOCUMENTS 1943777  9/1970  Fed. Rep. of Germany .

Primary Examiner—Richard L. Raymond
Attorney, Agent, or Firm—John W. Hogan, Jr.

[57] ABSTRACT

A method for the preparation of 4'-(substituted)-amino-2-(substituted)amino-3',5'-dichloroacetophenone and salts thereof. The method involves the chlorination of the corresponding 4'-(substituted)amino-2-(substituted) aminoacetophenone and acid addition salts thereof in the presence of an anhydrous or aqueous solvent selected from ethyl alcohol, t-butyl alcohol and acetic acid. The invention describes the preparation of 4'-amino-2-(t-butylamino)-3',5'-dichloroacetophenone and the hydrochloride thereof.

5 Claims, No Drawings

METHOD FOR THE PREPARATION OF 4'-(SUBSTITUTED)-AMINO-2-(SUBSTITUTED) AMINO-3',5'-DICHLOROACETOPHENONE AND SALTS THEREOF

This is a continuation of application Ser. No. 06/462,745, filed Feb. 1, 1983, now abandoned.

The invention is a process for the preparation of compounds of formula (I)

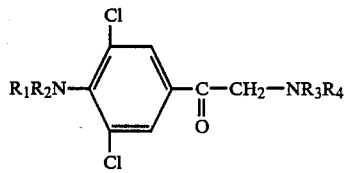

wherein $R_1$ is hydrogen or $C_1$–$C_{14}$ alkyl; $R_2$ is hydrogen or methyl and with the proviso that when $R_1$ is $C_2$–$C_{14}$ alkyl then $R_2$ is hydrogen; $R_3$ and $R_4$ each is hydrogen or $C_1$–$C_{12}$ alkyl. The compounds of formula (I) are useful and valuable intermediates for the preparation of biologically active 1-aminodichlorophenyl-2-aminoethanols of the formula (II)

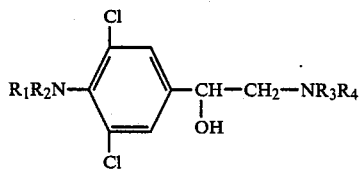

and salts thereof, wherein $R_1$ to $R_4$ are as hereinabove defined.

Certain compounds, related to those of formula (II) and the acid addition salts thereof are disclosed in U.S. Pat. No. 3,536,712, issued on Oct. 27, 1970. Specifically, patentees disclose methods for the synthesis of said compounds and state that said compounds are useful for enhancing the blood circulation, and as bronchodilators, analgesics, sedatives, antipyretics, antiphlogistics and antitussives in warm-blooded animals.

Other related 1-aminodihalophenyl-2-aminoethanols and their derivates are disclosed in Japanese Kokai 77 83,619 (Chemical Abstracts, 87, 201061r), German Offenlegungsschrift 2,804,625 (1979), German Offenlegungsschrift 2,157,040 (1973), German Offenlegungsschrift 2,261,914 (1974), European Patent Application 8,715 (1980), Netherlands Patent Application 7,303,612 (1973). These applications disclose uses of these compounds as analgesics; broncholytic, antiinflammatory, uterine spasmolytic, β-mimetic and/or β-blocking activities; antispasmolytic activity on cross-striped muscle structure; for tocology; reducing blood pressure by peripheral vasodilation and mobilizing body fat; and for treating allergies.

European Patent Application 26,298 (1979) discloses the use of such compounds for animal growth promotion and for increasing lean meat deposition and for improving lean meat to fat ratio.

As stated above, the compounds of formula (II)

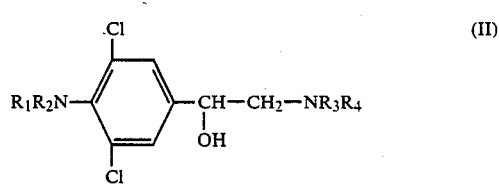

wherein $R_1$ to $R_4$ are hereinabove defined, are biologically active and are especially suitable for animal growth promotion and for improving lean meat to fat ratio. Among the compounds of formula (II), the compound (IIa)

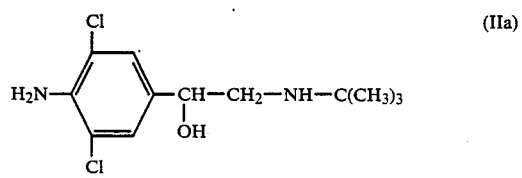

is of particular interest as an animal growth regulant and for improving lean meat to fat ratio.

In general, compounds of formula (II) may be prepared by the reduction of the corresponding ketone of formula (I). A reaction sequence resulting in the above defined formula (II) compounds may be described as follows: an aminoketone of formula (III) or an acid addition salt thereof is chlorinated in the presence of a solvent, to yield a formula (I) ketone of the invention; which in turn is then reduced to yield the corresponding, biologically active alcohol (or a salt thereof) of formula (II). The reaction sequence is hereinbelow graphically illustrated:

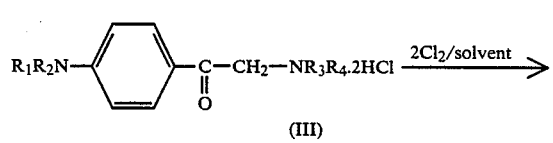

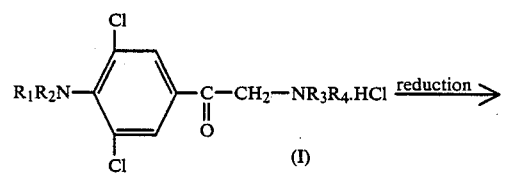

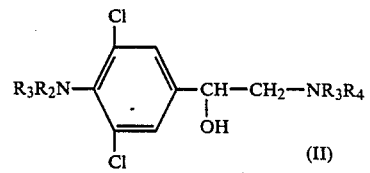

wherein in the above sequence $R_1$ is hydrogen or $C_1$–$C_{14}$ alkyl; $R_2$ is hydrogen or methyl, with the proviso that when $R_1$ is $C_2$–$C_{14}$ alkyl then $R_2$ is hydrogen; $R_3$ and $R_4$ each is hydrogen or $C_1$–$C_{12}$ alkyl. Among the dichloroketones of formula (I), the most preferred compound is 4'-amino-2-t-butylamino-3'5'-dichloroacetophenone of formula (Ia)

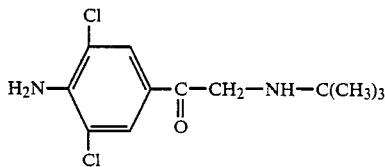

(Ia)

It should be noted here, that the preparation of the analogous 4'-amino-2-dimethylamino-3',5'-dibromoacetophenone is alluded to in U.S. Pat. No. 3,536,712 although no specific conditions and/or details are given for the preparation of this compound, or for its chlorinated congeners. The same patent disclosed conditions for the bromination of 4'-amino-2-(substituted amino)benzyl alcohol mono and dihydrochlorides in 50% to 100% acetic acid. This method is useful for the bromination of 4'-amino-2-[(t-butylamino)methyl]benzyl alcohol to afford the corresponding 4'-amino-2-[(t-butylamino)methyl]-3',5'-dibromobenzyl alcohol.

Chlorination, however, in the like manner does not appear to afford any substantial amount of 4'-amino-2-[(t-butylamino)methyl]-3',5'-dichlorobenzyl alcohol, instead side products such as trichloroaniline predominate. Likewise, chlorination of the corresponding ketone in 50% to 100% acetic acid also results in the formation of large amounts of side products such as trichloroaniline, which interferes with the purification of desired product. Furthermore, the chlorination in aqueous acetic acid is difficult to reproduce in satisfactory yields.

We now find, that by the method and process of the invention a ketone of formula (III), preferably its acid addition salt

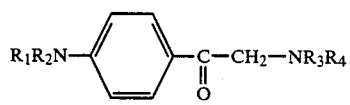

(III)

wherein $R_1$ is hydrogen or $C_1$–$C_{14}$ alkyl; $R_2$ is hydrogen or methyl and with the proviso that when $R_1$ is $C_2$–$C_{14}$ alkyl then $R_2$ is hydrogen; $R_3$ and $R_4$ each is hydrogen or $C_1$–$C_{12}$ alkyl; may be converted to the desired dichloro analog of formula (I) as follows: one molar equivalent of said formula (III) ketone, preferably its acid addition salt, such as the dihydrochloride, is dissolved in anhydrous ethyl or t-butyl alcohol and from about 2.0 to about 2.5 molar equivalents and preferably from about 2.0 to about 2.25 molar equivalents of chlorine gas is bubbled into the solution at a temperature range of from about 0° C. to about 20° C. and preferably from about 0° C. to about 10° C. at such a rate and over a sufficient period of time to essentially complete the reaction. The thus obtained compound of formula (I)

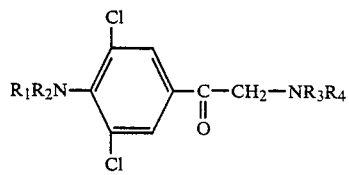

(I)

wherein $R_1$ to $R_4$ are hereinabove defined, may be purified if necessary or desired, by standard laboratory procedures such as recrystallization or column chromatography and then reduced to yield the biologically active alcohol of formula (II)

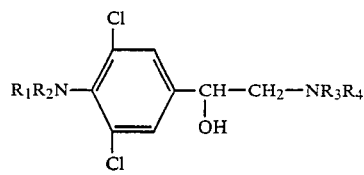

(II)

wherein $R_1$ to $R_4$ are as hereinabove described.

Advantageously, the preferred 4'-amino-2-t-butylamino-3',5'-dichloroacetophenone of formula (Ia) may be prepared by the above method in satisfactory yields and purity. Thus, the dihydrochloride of the above compound is dissolved in anhydrous ethyl or t-butyl alcohol and from about 2.0 to about 2.5 molar equivalent and preferably from about 2.0 to about 2.25 molar equivalent of chlorine gas is bubbled into the solution at a temperature range of from about 0° C. to about 20° C. and preferably 0° C. to about 10° C., over a period of time sufficient to essentially complete the reaction. The reaction may be graphically illustrated as follows:

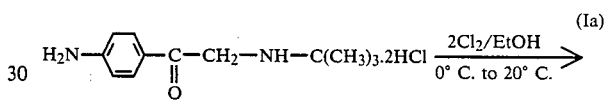

(Ia)

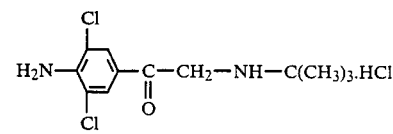

The thus obtained 4'-amino-2-(t-butylamino)-3',5'-dichloroacetophenone is then reduced by suitable means, as with sodium borohydride, to the desired alcohol of formula (IIa)

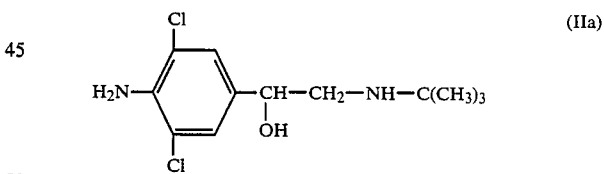

(IIa)

As stated above, the compounds of formula (II) and especially (IIa) are useful animal growth regulants and are effective for increasing lean meat deposition and for improving lean meat to fat ratio in poultry, swine, sheep, goats, domestic pets and cattle.

Animal feed compositions effective as animal growth regulants and effective for increasing lean meat deposition and for improving lean meat to fat ratio are generally prepared by admixing a formula (II) phenylethane derivative or acid addition salt thereof or an animal feed supplement containing said compound with a sufficient amount of animal feed to provide from about 0.1 to 1.0 ppm and preferably 0.1 to 0.5 ppm of said compound in the feed.

Anima feed supplements can be prepared by admixing about 75% to 95% by weight of a formula (II) phenylethane derivative or acid addition salt thereof with about 5% to 25% by weight of a suitable carrier or diluent, selected from the group consisting of alfalfa meal, soybean meal, cottonseed oil meal, linseed oil meal, sodium chloride, cornmeal, cane molasses, urea, bone meal, corncob meal and the like.

The preferred medicated swine, cattle, sheep and goat feeds generally contain from 0.01 to 100 grams of active ingredient per ton of feed, the optimum amount for these animals usually being about 0.3 to 50 grams per ton of feed.

The preferred poultry and domestic pet feeds usually contain about 0.01 to 100 grams and preferably 0.3 to 50 grams of active ingredient per ton of feed.

The invention is further illustrated by the non-limiting Examples set forth below.

EXAMPLE 1

Preparation of
4'-amino-2-(t-butylamino)-3',5'-dichloroacetophenone dihydrochloride Chlorine gas (14.2 g; 0.20 mol, in 25% excess over theory) is bubbled into a solution of 4'-amino-2-(t-butylamino)acetophenone dihydrochloride (24.8 g of 90% pure=22.34 g real; 0.08 mol) in absolute (dry) ethanol (160 ml) at 5° C. over a one to two hour period of time. The reaction mixture is then evaporated to dryness under vacuum and the residue is slurried in acetone (160 ml), filtered and dried to afford the product, 22.5 g of a pale yellow solid containing approximately 5% by weight of water (yield: 21.37 g, or 85.7% of theory), mp 255°–257° C.

Proton NMR: δ CD$_3$OD [1.50(S, 9H, CH$_3$—); 4.56 (S, 2H, —CH$_2$—); 4.80 (S, 4H, exchangeable protons); 7.90 (S, 2H, aromatics)].

IR: Ketone carbonyl stretching frequency at 1640 cm$^{-1}$; amine NN stretching frequency at 3200 cm$^{-1}$.

EXAMPLE 2

Preparation of
4'-amino-2-(t-butylamino)-3',5'-dichloroacetophenone hydrochloride using various solvent systems By the method of Example 1, a number of reactions are performed using various solvents (and combinations) to evaluate the effect of same on the yields of the product. The results are summarized in Table I below.

TABLE I

The effect of various solvents (and mixtures thereof) on the yields of 4'-amino-2-(t-butylamino-3',5'-dichloroacetophenone

| No | Reaction solvent, or solvent mixture | Percent* yield | Comments |
|---|---|---|---|
| 1 | Water | — | tars formed |
| 2 | Ethanol:water; 3:1 | 49.0 | off white solid |
| 3 | Ethanol:water; 19:1 | 75.5 | product clean by TLC |
| 4 | Ethanol - dry | 90.3 | pale yellow; extremely clean by TLC |
| 5 | Ethanol - dry | 86.0 | clean by TLC and NMR |
| 6 | t-butanol - dry | 74.0 | the reaction temperature was 27° C. |
| 7 | Acetic acid:water; 1:1 | 65.0 | trichloroaniline by-product present |
| 8 | Acetic acid:water; 1:1 | 49.0 | trichloroaniline by-product present |
| 9 | Formic acid:water; 1:1 | 39.0 | |
| 10 | 19% hydrochloric acid | 50.0 | product discolored (gray) |
| 11 | CH$_2$Cl$_2$ | — | starting material + |

TABLE I-continued

The effect of various solvents (and mixtures thereof) on the yields of 4'-amino-2-(t-butylamino-3',5'-dichloroacetophenone

| No | Reaction solvent, or solvent mixture | Percent* yield | Comments |
|---|---|---|---|
| | | | some product |

\* = The purity of the products obtained in these reactions were not taken into consideration when calculating yields.

EXAMPLE 3

Preparation of various substituted amino-3',5'-dichloroacetophenones

By the method described in Example 1, the following useful products are obtained from their corresponding precursors:

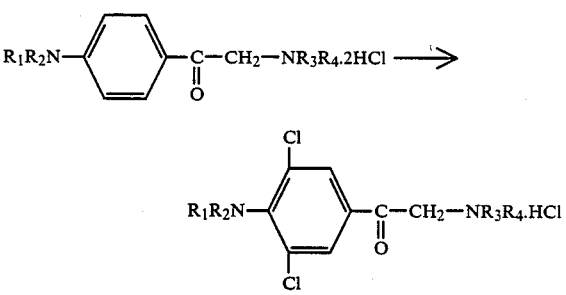

wherein,

| R$_1$ | R$_2$ | R$_3$ | R$_4$ |
|---|---|---|---|
| H | CH$_3$ | H | t-butyl |
| H | H | H | i-propyl |
| H | Et | H | t-butyl |
| H | H | H | n-propyl |
| H | H | i-propyl | i-propyl |
| H | H | H | ethyl |

What is claimed is:

1. A method for the preparation of a first compound of structural formula

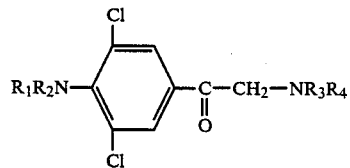

wherein R$_1$ is hydrogen or C$_1$–C$_{14}$ alkyl; R$_2$ is hydrogen or methyl, with the proviso that when R$_1$ is C$_2$–C$_{14}$ alkyl then R$_2$ is hydrogen; and R$_3$ and R$_4$ are hydrogen or C$_1$–C$_{12}$ alkyl or an acid addition salt thereof which comprises chlorinating one molar equivalent of a second compound of structural formula

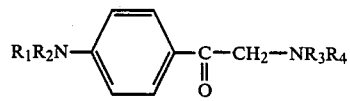

wherein R$_1$–R$_4$ are as hereinabove defined for said first compound, or an acid addition salt thereof with about 2.0 to 2.5 molar equivalents of chlorine at a temperature from about 0° to 20° C. and in a solvent system consisting essentially of anhydrous or aqueous ethyl alcohol or t-butyl alcohol for a period of time sufficient to form said first compound.

2. A method according to claim 1, wherein $R_1$ and $R_2$ are hydrogen; and $R_3$ and $R_4$ are hydrogen or $C_1$–$C_4$ straight or branched-chain alkyl.

3. A method according to claim 2, wherein the first compound is 4'-amino-2-(t-butylamino)-3',5'-dichloroacetophenone.

4. A method according to claim 3, wherein the acid addition salt of the compound to be chlorinated is the dihydrochloride; the temperature range is 0° to 10° C.; and the solvent is anhydrous ethyl alcohol or t-butyl alcohol.

5. A method according to claim 4, wherein 4'-amino-2-(t-butylamino)acetophenone dihydrochloride is chlorinated with 2.0 to 2.5 molar equivalent of chlorine gas in anhydrous ethyl alcohol.

* * * * *